US00PP33367P2

(12) United States Plant Patent
Hansen

(10) Patent No.: US PP33,367 P2
(45) Date of Patent: Aug. 17, 2021

(54) ***ORIGANUM* PLANT NAMED 'DROPS OF JUPITER'**

(50) Latin Name: *Origanum vulgare*
Varietal Denomination: Drops of Jupiter

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,231

(22) Filed: Nov. 19, 2020

(51) Int. Cl.
*A01H 5/02* (2018.01)
*A01H 6/50* (2018.01)

(52) U.S. Cl.
USPC ..... Plt./258

(58) Field of Classification Search
USPC ..... Plt./258
CPC ... A01H 5/12; A01H 5/02; A01H 5/00; A01H 6/50
See application file for complete search history.

(56) References Cited

PUBLICATIONS

Digger Magazine Farwest New Varieties Showcase 2020, retrieved on Mar. 18, 2021, retrieved from the Internet at http://www.diggermagazine.com/wp-content/uploads/2020/08/New-Varieties-2020-Final.pdf, pp. 34-48. (Year: 2020).*

* cited by examiner

*Primary Examiner* — June Hwu

(57) ABSTRACT

The new and distinct hardy perennial plant, *Origanum* 'Drops of Jupiter', has dense, rounded, habit with mostly upright to slightly outwardly stems. The foliage is ovate, and chartreuse-yellow and resists burning when planted in full sun. Flowering begins in early summer and continues to early fall or frost with mauve-pink petal colors with persistent purple calyces. The new plant is attractive and useful in the landscape en masse, as an accent, or in containers.

1 Drawing Sheet

Botanical denomination: *Origanum vulgare.*
Variety designation: 'Drops of Jupiter'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Feb. 2, 2020. Subsequently, the new plant was advertised in the "Walters Gardens 20-21 Catalog" by Walters Gardens, Inc. released on May 20, 2020. The claimed plant was first sold to the public on Aug. 23, 2020 by Walters Gardens, Inc., who obtained the plant and all information relating thereto, from the inventor. No plants of *Origanum* 'Drops of Jupiter' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Origanum* named 'Drops of Jupiter'. The new plant resulted from a self-pollination by the inventor of the unreleased, unnamed, proprietary seedling named by breeder code 14-6-3 (not patented) as the female parent and the male parent on Jun. 30, 2015 at a wholesale perennial nursery in Zeeland, Mich. Seed was harvested in the summer of 2015 and given the breeder code 15-2-1 during the final trial stages of the summer of 2015. The new plant has been asexually propagated initially by division in fall of 2017 followed by shoot tip cuttings since the summer of 2018 with the resultant plants remaining identical to the original plant, stable and true to type in successive generations.

SUMMARY OF THE INVENTION

*Origanum* 'Drops of Jupiter' is different from its parents and all other Ornamental Oregano known to the inventor. The nearest comparison cultivars known to the inventor are 'Dr. Ietswaart' (not patented), which is one of the grandparents of the new plant and 'Aurea' (not patented). 'Dr. Ietswaart' has a broader habit and the flowers are very pale lavender to white. 'Aurea' is more upright in habit and the flowers are paler pink with less significant bracts. The selfed parent, 14-6-3, is taller and looser in habit. Another grandparent, 'Lizzie' has green foliage with longer inflorescence with lighter lavender-pink flower. Compared with 'ALL120506' U.S. Plant Pat. No. 29,589 the new plant has smaller chartreuse foliage and smaller flowers and calyces. 'Bellisimo' U.S. Plant Pat. No. 27,353 has deeper colored flower bracts and the foliage is a deep olive green.

The present invention has not been evaluated under all possible environmental conditions. The phenotype may vary with changes in the environment such as light, temperature, water and nutrient availability, etc. without a change in the genotype of the plant. *Origanum* 'Drops of Jupiter' is unique from all other Ornamental Oregano known to the inventor in the following combined traits:

1. The habit is dense, rounded, mound with mostly upright to slightly outright stems spreading with maturity.

2. Foliage is ovate and chartreuse yellow when planted in full sun and resist burning.
3. Flowers are mauve-pink with showy and persistent purple calyces.
4. Flowers beginning in early summer and continues into early fall or until frost.

BRIEF DESCRIPTION OF THE DRAWINGS

The photographs of the new plant *Origanum* 'Drops of Jupiter' are of a two-year-old plant in a full sun trial garden in Zeeland, Mich. and demonstrate the unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
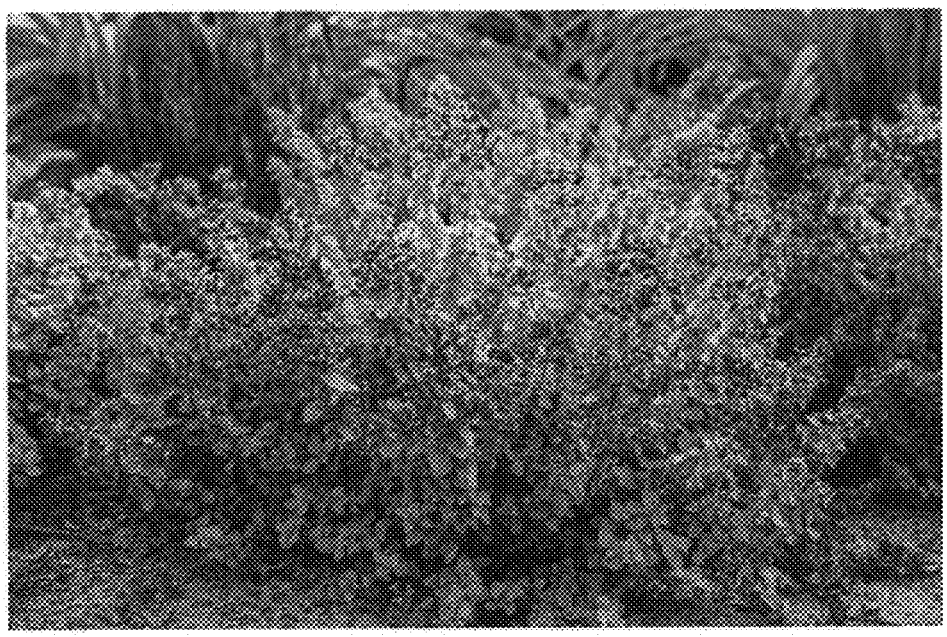
FIG. 1 shows the overall habit of the new plant in mid-season flower.
Figure 2:
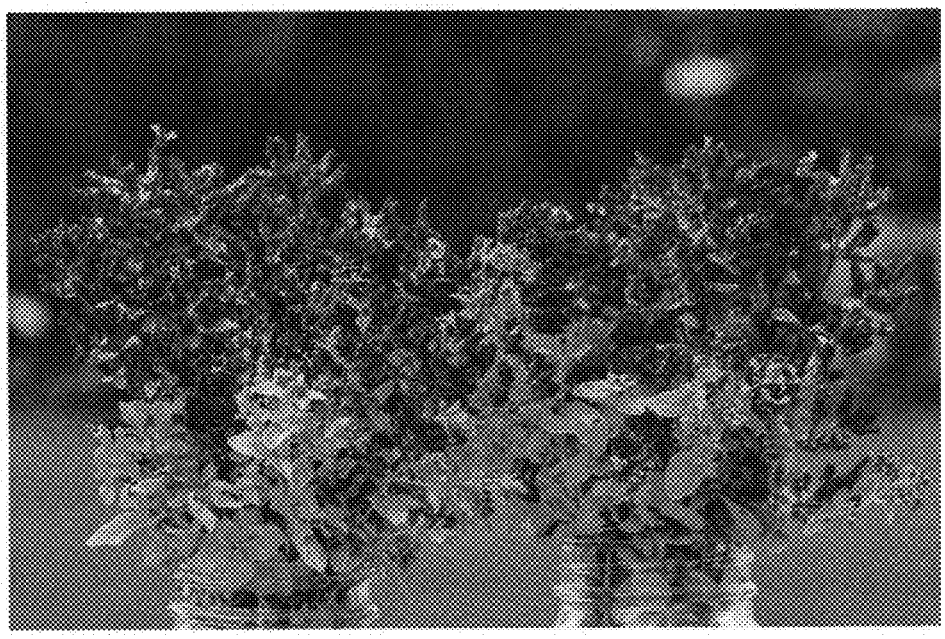
FIG. 2 shows a close-up of the flowers and buds on cut stems.

The following descriptions are based on a two-year-old plant of *Origanum* 'Drops of Jupiter' grown in a full-sun display garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: Proprietary unnamed seedling selection known only by the breeder code 14-6-3 as the female or seed parent and also the male or pollen;

Plant habit: Herbaceous perennial; sprawling mound to about 39 cm tall and 82 cm wide at the soil level when in peak flower;

Growth: Rapid; finishing in a standard #1-15 cm container in about 10 to 12 weeks from rooted plug; time to initiate roots at 23° C. about one to two weeks;

Root: Fine, freely branching; color nearest RHS 155D depending on soil type and nutrient content;

Foliage: Opposite; simple; ovate; acute apex; attenuate to slightly oblique base; margin entire to micro-ciliolate; sparsely puberulent adaxial and glabrous abaxial; adaxial and abaxial surface matte; distal cauline foliage sessile;

Leaf size: Blade size about 27.0 mm long and 18.0 mm wide; distal cauline foliage decreasing in size;

Leaf color: Young adaxial nearest RHS 144A, young abaxial between RHS 145A and RHS 138B; mature adaxial variable comprising RHS 161D, RHS 144A and between RHS 144A and RHS N144A, mature abaxial variable comprising RHS 146D, RHS 146C and RHS 161D;

Leaf fragrance: Pleasantly spicy; strongly aromatic;

Venation: Pinnate; glabrous; slightly impressed on adaxial surface and ribbed on abaxial surface;

Vein color: And between RHS 144A and RHS N144A on adaxial surface and nearest RHS 146D on abaxial surface;

Petiole: Flat; puberulent adaxial and abaxial; sessile on distal foliage;

Petiole size: To 9.0 mm long and 2.0 mm wide at base;

Petiole color: Nearest RHS 145C adaxial and abaxial;

Stem: About 36 main stems per plant; micro-puberulent; quadrangular, about 4.5 mm across at base and to about 51.0 cm long; upright to outwardly; heavily branched at about the distal 14 nodes; to about 28 branches of up to about 13.0 cm long and about 1.0 mm across at base, decreasing distally; branch angle about 45 to 50 degrees below vertical;

Internodes: About 21 per stem; average about 2.4 cm apart with greatest distance in the middle of the stem;

Stem color: Young actively growing nearest RHS 145C, older distal portion nearest RHS 187A, proximal portion nearest RHS N202A; node color typically same as surrounding stem;

Inflorescence: Compact cyme with small ornamental bracts subtending individual flowers; to about 18 flowers per branchlet; flowering in distal 28.0 cm to about 19.0 cm wide;

Flowering season: From about early-summer to early fall;

Peduncle: Mostly vertical, puberulent; cylindrical; stiff; strong; to about 2.5 cm long and 0.2 cm diameter; with about 18 flowers;

Peduncle color: Nearest RHS 187C;

Pedicel: Sessile;

Flower bud: Obovate; about 4.0 mm long and 1.2 mm wide near apex one day prior to opening; abaxial calyx;

Flower bud color: Petal portion nearest RHS 75B, calyx proximal portion nearest RHS 145A, distally nearest RHS 187B;

Flowers: Zygomorphic; bilabiate; about 8.0 mm long to exserted pistil, about 3.5 mm wide at lower lip and 3.0 mm tall; sympetalous with basal 4.0 mm fused; bisexual or lacking androecium; synsepalous;

Corolla: About 6.0 mm long and 3.5 mm wide and 3.0 mm tall; fused tube portion about 4.0 mm long and 2.0 mm diameter at fusion and 1.0 mm diameter at base;

*Upper lip*.—Tri-lobed; center lobe rounded apex and entire margin, about 1.0 mm long and 1.0 mm wide; two side lobes rounded apex and entire margin, about 1.0 mm long and 0.7 mm wide.

*Upper lip color*.—Initially adaxial and abaxial nearest RHS 75B distally with base nearest RHS NN155D, at maturity and before dropping adaxial and abaxial nearest RHS 77C distally with basal 2.0 mm of corolla tube nearest RHS NN155D.

*Lower lip*.—Bi-lobed; each lobe rounded apex and entire margin; to about 1.7 mm long and 1.0 mm wide.

*Lower lip color*.—Initially adaxial and abaxial nearest RHS 75B distally with base nearest RHS NN155D, at maturity and before dropping adaxial and abaxial nearest RHS 77C distally with basal 2.0 mm of corolla tube nearest RHS NN155D.

Calyx: Synsepalous; campanulate; 5-merous fused into calyx tube; 2.0 mm long and 1.0 mm across;

Sepals: Five; glabrous; fused in basal 1.5 mm and separated in distal 0.5 mm; acute apex, base fused; persistent; about 2.0 mm long and 0.5 mm across at fusion;

Sepal color: Adaxial and abaxial base nearest RHS 145A, adaxial and abaxial apices nearest RHS 187B;

Bracts: Below each flower and branch; ovate, acute margin, attenuate base, glabrous adaxial and abaxial; to about 5.0 mm long and 3.0 mm across near middle;

Bract color: Adaxial and abaxial the same; nearest RHS 144A proximally and distally nearest RHS 187B;

Gynoecium: Single; 8.0 mm long;

*Style*.—Cylindrical; glabrous; about 5.5 mm long and 0.3 mm diameter; color in basal portion nearest RHS 75D, distally before stigma between RHS 64B and RHS 64C.

*Stigma*.—Bifid; about 0.7 mm long; color nearest RHS 64A.

*Ovary*.—Superior; globose; about 0.5 mm diameter; ovary color nearest RHS 145B.

Androecium: Four;

*Anthers*.—Basifixed; globose; about 0.2 mm diameter; color nearest RHS 202A.

*Filaments*.—Adnate inner corolla tube; various lengths from about 1.0 mm to 5.0 mm and about 0.1 mm diameter; color nearest RHS NN155D.

*Pollen*.—Not observed.

Flower fragrance: No distinct fragrance detected from flowers;

Fruit and seed: Not observed;

Pest and disease: Susceptibility or resistance beyond that which is typical for *Origanum* but typically not prone to browsing by deer or rodents. The new plant has not been found to be susceptible to bacterial or fungal leaf spots. The foliage resists burning in full sun.

Hardiness: Hardy from USDA zones 4 through 9.

I claim:

1. The new and distinct hardy perennial plant, *Origanum* 'Drops of Jupiter' essentially as herein described and illustrated.

* * * * *